US005827682A

United States Patent [19]
Bryan et al.

[11] Patent Number: 5,827,682
[45] Date of Patent: Oct. 27, 1998

[54] TWO-STEP CONVERSION OF VEGETABLE PROTEIN ISOFLAVONE CONJUGATES TO AGLUCONES

[75] Inventors: Barbara A. Bryan, University City, Mo.; Maryann C. Allred, Collinsville, Ill.; Mark A. Roussey, Chesterfield, Mo.

[73] Assignee: Protein Technologies International, Inc., St. Louis, Mo.

[21] Appl. No.: 730,171

[22] Filed: Oct. 15, 1996

Related U.S. Application Data

[63] Continuation-in-part of Ser. No. 477,102, Jun. 7, 1995, abandoned.

[51] Int. Cl.$^6$ .............................. C21P 21/06; C12N 9/24; C07D 311/64
[52] U.S. Cl. ........................ 435/68.1; 435/75; 435/125; 435/200; 435/272; 549/402; 549/403
[58] Field of Search ................................. 435/125, 68.1; 549/403

[56] References Cited

U.S. PATENT DOCUMENTS

| | | | |
|---|---|---|---|
| 3,391,001 | 7/1968 | Sair et al. | 99/17 |
| 3,461,205 | 8/1969 | Mansfeld et al. | 424/195 |
| 3,870,805 | 3/1975 | Hayes et al. | 426/148 |
| 3,949,085 | 4/1976 | Feuer et al. | 424/283 |
| 4,064,277 | 12/1977 | Yokotsuka et al. | 426/331 |
| 4,157,984 | 6/1979 | Zilliken | 252/407 |
| 4,163,746 | 8/1979 | Feuer et al. | 260/345.2 |
| 4,218,489 | 8/1980 | Zilliken | 426/545 |
| 4,232,122 | 11/1980 | Zilliken | 435/52 |
| 4,259,358 | 3/1981 | Duthie | 426/46 |
| 4,264,509 | 4/1981 | Zilliken | 260/345.2 |
| 4,366,082 | 12/1982 | Zilliken | 252/404 |
| 4,366,248 | 12/1982 | Zilliken | 435/125 |
| 4,390,559 | 6/1983 | Zilliken | 426/545 |
| 4,428,876 | 1/1984 | Iwamura et al. | 260/123.5 |
| 4,841,077 | 6/1989 | Ito et al. | 549/402 |
| 4,889,921 | 12/1989 | Diosady et al. | 530/377 |
| 4,960,908 | 10/1990 | Ito et al. | 549/403 |
| 5,141,746 | 8/1992 | Fleury et al. | 424/195.1 |
| 5,320,949 | 6/1994 | Shen et al. | 435/68.1 |

FOREIGN PATENT DOCUMENTS

| | | |
|---|---|---|
| 258669 | 12/1989 | Japan . |
| 1514765 | 10/1989 | U.S.S.R. . |
| WO9510512 | 4/1995 | WIPO . |
| WO9510529 | 4/1995 | WIPO . |
| WO9510530 | 4/1995 | WIPO . |

OTHER PUBLICATIONS

"Proceedings Of The American Association For Cancer Research", vol. 34, Mar. 1993, Abstracts 99 and 3310.

"Genistein And Biochanin A Inhibit The Growth Of Human Prostate Cancer Cells But Not The Epidermal Growth Factor Receptor Tyrosine Autophosporylation", by Peterson and Barnes: *The Prostate*, 22:335–345 (1993).

"Soybeans Inhibit Mammary Tumors In Models Of Breast Cancer", by Barnes et al., *Mutagens and Carcinogens in the Diet*, pp. 239–253 (1990).

"Genistein Inhibition Of The Growth Of Human Breast Cancer Cells: Independence From Estrogen Receptors And The Multi–Drug Resistance Gene", by Peterson and Barnes, Biochemical and Biophysical Research Communications, vol. 179, No. 1, pp. 661–667, 1991.

"Genistein, A Specific Inhibitor Of Tyrosine–Specific Protein Kinases", by Akiyama et al., *The Jry of Biological Chemistry*, vol. 262, No. 12, pp. 5592–5595 1987.

"Mechanisms Of Action In NIH–3T3 Cells Of Genistein, An Inhibitor of EGF Receptor Tyrosine Kinase Activity", by Linassier et al., *Biochemical Pharmacology*, vol. 39, No. 1, pp. 187–193 (1990).

"The Role Of Soy Products In Reducing Risk Of Cancer", by Messina and Barnes, *Journal of the National Cancer Institute*, vol. 83, No. 8, pp. 541–546 (1991).

"Effect Of Genistein On Topoisomerase Activity And On the Growth Of [VAL 12] Ha–ras–Transformed NIH 3T3 Cells", by Okura et al., *Biochemical and Biophysical Research Communications*, vol. 157, No. 1, pp. 183–189, (1988).

"Induction Of Mammalian Topoisomerase II Dependent DNA Cleavage By Nonintercalative Flavanoids, Genistein And Orobol", by Yamashita et al., *Biochemical Pharmacology*, vol. 39, No. 4, pp. 737–744 (1990).

"Soybean Utilization", pp. 64–66 (1987).

"Soybeans: Chemistry And Technology", pp. 187–188 (1978).

"B–Glucosidase From, Soybeans Hydrolyze Daidzin And Genistin", by Matsuura, et al., *Journal of Food Science*, vol. 58, No. 1, pp. 144–147 (1993).

"Proposed Draft Standard For Soy Protein Products", Report of the Fifth Session of the Codex Committee on Vegetable Proteins, Ottawa, Canada, Feb. 6–10, 1989.

"Isoflavone Composition of American And Japanese Soybeans In Iowa: Effects Of Variety, Corp Year, And Location", by Heui–ju Wang and Patrica A. Murphy, *J. Agric. Food Chem.*, vol. 42, pp. 1666–1673 (1974); pp. 1674–1677, 1974.

"Objectionable Flavor Of Soy Milk Developed During The Soaking Of Soybeans And Its Control", by Matsuura et al., *J. of Food Science*, vol. 54, No. 3, pp. 602–605 1989.

(List continued on next page.)

*Primary Examiner*—Deborah C. Lambkin
*Assistant Examiner*—Taofiq A. Solola
*Attorney, Agent, or Firm*—Richard B. Taylor

[57] ABSTRACT

Disclosed are methods for converting isoflavone conjugates in vegetable protein materials to isoflavone aglucones by forming an aqueous mixture of a vegetable protein material containing isoflavone conjugates, converting the isoflavone conjugates to isoflavone glucones, and converting the isoflavone glucones to isoflavone aglucones. The vegetable protein material may also contain isoflavone glucones which are converted to isoflavone aglucones. The isoflavone conjugates, isoflavone glucones, or isoflavone aglucones present in the vegetable protein material may be removed from the vegetable materials before, during, or after the conversion process.

34 Claims, No Drawings

OTHER PUBLICATIONS

"B–Galactosidase–Inhibiting New Isoflavanoids Produced By Actinomycetes", by Hazato et al., *The Journal of Antibiotics*, vol. XXXII, No. 3, pp. 217–222 (1979.

"A Specific Inhibitor For Tyrosin Protein Kinase From Pseudomonas", by Ogawara et al., Ogawara et al., *The Jou. of Antibiotics*, vol. XXXIX, No. 4, pp. 606–608 1986.

"Control Of Serum Lipids With Soy Protein", by J. Erdman, *The New England Journal of Medicine*, vol. 333, No. 5, pp. 313–314 (1995).

*The Flavanoids, Advances In Research Since 1980*, pp. 125–209 (ed. by J. Harborne 1988).

TWO-STEP CONVERSION OF VEGETABLE PROTEIN ISOFLAVONE CONJUGATES TO AGLUCONES

This is a continuation-in-part application of application Ser. No. 08/477,102, filed Jun. 7, 1995, abandoned.

FIELD OF THE INVENTION

The present invention relates to a two-step process for converting isoflavone conjugates in vegetable protein materials to isoflavone aglucones. In addition, the present invention relates to the resulting products containing isoflavone aglucones.

BACKGROUND OF THE INVENTION

Isoflavones occur in a variety of leguminous plants, including vegetable protein materials such as soybeans. These compounds include daidzin, 6"-OAc daidzin, 6"-OMal daidzin, daidzein, genistin, 6"-OAc genistin, 6"-OMal genistin, genistein, glycitin, 6"-OAc-glycitin, 6"-OMal gylcitin, glycitein, biochanin A, formononetin, and coumestrol. Typically these compounds are associated with the inherent, bitter flavor of soybeans. In the production of commercial products, such as isolates and concentrates, the focus has been to remove these materials. For example, in a conventional process for the production of a soy protein isolate in which soy flakes are extracted with an aqueous alkaline medium, much of the isoflavones are solubilized in the extract, and remain solubilized in the extract, which is usually discarded following acid precipitation of the protein to form an isolate. Residual isoflavones left in the acid precipitated protein isolate are usually removed by exhaustive washing of the isolate.

It has recently been recognized that the isoflavones contained in vegetable proteins such as soybeans may inhibit the growth of human cancer cells, such as breast cancer cells and prostrate cancer cells, as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research. Communications*, Vol. 179, No. 1, pp. 661–667, Aug. 30, 1991; "Genistein and Biochanin A Inhibit the Growth of Human Prostate Cancer Cells but not Epidermal Growth Factor Receptor Tyrosine Autophosphorylation" by Peterson and Barnes, The Prostate, Vol. 22, pp. 335–345 (1193); and "Soybeans Inhibit Mammary Tumors in Models of Breast Cancer" by Barnes, et al., *Mutagens and Carcinogens in the Diet*, pp. 239–253 (1990).

Of the above isoflavones, several exist as glucosides, or as glucones, with a glucose molecule attached. Several of the glucones such as the 6"-OAc genistin or the 6"-OMal genistin, contain an acetate group or a malonyl group, respectively, attached to the six position of the glucose molecule itself. Compounds of this type, i.e. having additional moieties attached to the glucose moiety, are generally referred to as "conjugates". While all the isoflavones, including the glucosides, are of interest in medical evaluation, the specific isoflavones of most interest are the aglucones, which have no attached glucose moiety. Specific isoflavones in this category are daidzein, genistein, and glycitein. These aglucones have the following general formula:

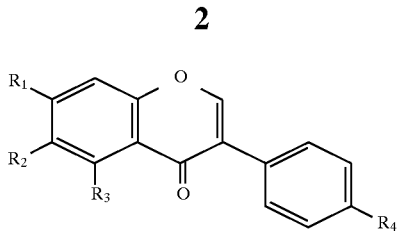

wherein, $R_1$, $R_2$, $R_3$ and $R_4$ may be selected from the group consisting of H, OH and $OCH_3$. It is therefore to the aglucones and enrichment of a vegetable protein material with these materials to which the present invention is directed.

Methods are known in the art for converting glucone isoflavones to aglucone isoflavones, such as described in the published Japanese Patent Application 258,669 to Obata et al. Such processes achieve only a moderate extent of conversion and so are not desirable, particularly for large scale commercial operations. In addition, known processes such as described in the '669 application teach removing the isoflavones from the protein material and do not describe how to prepare an aglucone isoflavone enriched vegetable protein material.

Processes are also known for producing specific aglucone isoflavone enriched vegetable protein derivatives such as protein extracts, protein whey, and protein concentrate products by conversion of isoflavone glucones to isoflavone aglucones, such as described in currently pending published patent applications PCT/US94/10697, PCT/US94/10699, and PCT/US94/10696, all owned by the assignee of the present application. Thus, there is a need for a process of converting at least a majority and preferably substantially all isoflavone conjugates to aglucone isoflavones, and for producing an aglucone isoflavone enriched vegetable protein material.

SUMMARY OF THE INVENTION

It is therefore an object of the present invention to provide an aglucone isoflavone enriched material, and a novel process for producing the same from a vegetable protein material containing isoflavone conjugates.

The present invention provides methods for converting isoflavone conjugates to isoflavone aglucones. A mixture comprising isoflavone conjugates and water is formed and treated at a pH of about 6 to about 13.5 and a temperature of about 2° C. to about 121° C. to convert a majority of the isoflavone conjugates to isoflavone glucones. Isoflavone glucones, either converted from the isoflavone conjugates or initally present in the mixture, are contacted with an enzyme capable of cleaving isoflavone glucoside bonds at a pH of about 3 to about 9 and a temperature of about 5° C. to about 75° C. to convert the isoflavone glucones in the mixture to isoflavone aglucones. The present invention includes variations of the process in which the respective isoflavone conjugates, isoflavone glucones, or isoflavone aglucones present in a vegetable protein material are removed from the vegetable materials before, during, or after the two-step conversion process.

DESCRIPTION OF THE PREFERRED EMBODIMENTS

The novel process is a two-step method for converting at least a majority of isoflavone conjugates to isoflavone aglucones. Preferably, the isoflavone conjugates are present in a vegetable protein or plant material. This process has been found to assure substantially full conversion of isoflavone conjugates and isoflavone glucones to isoflavone aglucones. The first step involves conversion of isoflavone conjugates to isoflavone glucosides, also referred to herein as isoflavone glucones. The second step involves conversion of the isoflavone glucones, either produced from the first step or initially present in the vegetable material, to isoflavone aglucones. In some vegetable protein materials, particularly soy protein materials, a substantial portion of the total isoflavone content in the vegetable protein material is present in the form of isoflavone conjugates, therefore, conversion of the isoflavone conjugates to isoflavone glucones prior to conversion of the isoflavone glucones to isoflavone aglucones can greatly increase amount of isoflavone aglucones available from the vegetable protein material.

The starting material of the preferred embodiment process is any vegetable protein or plant material comprising isoflavone conjugates. Although the preferred embodiment process will be described with respect to soybean products, the present process is generally applicable to a wide array of vegetable protein materials besides soy or soybean materials. Moreover, the term "soybean material" as used herein refers to soybeans or any type of soybean derivative.

There are several variant embodiments of the process of the present invention. In a first embodiment, the isoflavone conjugates are converted to isoflavone aglucone form while the isoflavone compounds remain the vegetable protein material. The thus produced isoflavone aglucones may be left in the vegetable protein material, or may optionally be removed. The aglucone forms of isoflavones may generally be removed by solvent or nonaqueous leaching or extraction methods. Suitable solvents for such operations include, but are not limited to acetone, ethanol, and other similar organic solvents. It is further contemplated that aqueous extraction methods could be used in some applications if the pH of the system is sufficiently basic such that the aglucone forms are readily soluble therein.

In a second embodiment, the isoflavone conjugates are converted to isoflavone glucones while in the vegetable protein material. The isoflavone glucones are then removed from the vegetable protein material by aqueous leaching or extraction methods. Aqueous leaching may be performed by soaking plant materials, or otherwise exposing or immersing plant materials in water or mixtures of other water compatible solvents such as ethanol or other alcohols to leach out the relatively soluble isoflavone glucones. The pH of the resulting aqueous system is from about 4 to about 11, and most preferably about 7. After removal, the isoflavone glucones are then converted to isoflavone aglucone form.

In a third embodiment, the isoflavone conjugates are removed from the vegetable protein material prior to performing any conversion operations. Since the conjugate form of isoflavones is relatively soluble in water, the isoflavone conjugates may be removed from the vegetable protein material by aqueous leaching or extraction methods, as previously described. After such removal, the isoflavone conjugates are then converted to the glucone form and then to the aglucone form.

Depending upon the type of vegetable plant material containing the isoflavone conjugates, it may be necessary in some instances to process the plant material into a finely divided form. This may be desirable to render the isoflavone compounds contained in the vegetable material accessible to the various reagents utilized in either or both the first and second steps, described in greater detail below. The material may be ground, crushed, or otherwise processed by conventional methods known in the art. If the plant material is in a state such that the isoflavone compounds in the plant material are readily accessible to external reagents or reactants, such as small leafy portions of certain plants, it may not be necessary to subject the plant material to such processing.

In the first conversion step or operation, isoflavone conjugates in the vegetable protein material are converted to isoflavone glucosides by chemical reaction. This reaction has been found to be particularly rapid and efficient at a particular combination of pH and temperature ranges. Preferably, the vegetable protein material is introduced into a reaction vessel, or other suitable container with a sufficient amount of water. The amount of water is not critical so long as a relatively uniform mixture or dispersion of the vegetable protein material is formed. The preferred pH range for the first conversion step is from about 6 to about 13.5. The conversion of isoflavone conjugates to isoflavone glucones has been found to be base catalyzed, and so it is most preferred to utilize a high pH to achieve rapid conversion. The most preferred pH for the first step is a pH of about 11. The pH may be adjusted by the addition of any suitable base, caustic agent, or basic reagent that will increase the pH of the system, such as sodium hydroxide.

The preferred temperature for the first step is about 2° C. to about 121° C. The most preferred temperature depends upon the pH. The inventors have found that the conversion can occur rapidly at lower temperatures when the pH is relatively high. At a pH of about 9 where the conversion occurs efficiently within a temperature range of about 45° C. to about 75° C., the most preferred temperature is about 73° C. At a pH of about 11, the preferred temperature is from about 5° C. to about 50° C., with 35° C. being particularly preferred. When the pH is relatively low, the conversion can occur at higher temperatures. For example, at a pH of about 6 the conversion can occur within a temperature range of about 80° C. to about 121° C.

It is preferred that the mixture be maintained at a relatively constant temperature throughout the entire period for the conversion from isoflavone conjugates to isoflavone glucones. In some instances, however, it may be desirable to increase or decrease the temperature over the course of the first step conversion.

The time period required for conversion of isoflavone conjugates to isoflavone glucosides in the first step depends primarily upon the pH and temperature range utilized. Such times typically range from about 15 minutes up to several hours or longer. Conversion can occur more rapidly at a higher pH and at a higher temperature. At a pH of about 9, conversion is substantially complete in about 4 to about 6 hours at about 73° C. In a particularly preferred embodiment, a specific combination of process parameters is utilized for the first step conversion. These parameters are a pH of about 11, a temperature of about 5° to about 50° C., and a conversion time of about 15 to about 45 minutes.

The first isoflavone conversion step is remarkably efficient, converting at least a majority, and preferably substantially all of the isoflavone conjugates to isoflavone glucones. The extent of conversion of isoflavone conjugates to isoflavone glucones during the first step is typically from at least about 80% up to 100%. By use of the preferred reaction parameters previously described it is possible to achieve conversions of 95% or more. These high conversion rates are particularly attractive for large scale commercial operations.

The inventors have found that it is most preferred to perform the first conversion step in an aqueous system. Other water compatible components may be present in the system such as certain alcohols, such as for example, methanol. Generally, the first conversion step does not require frequent mixing nor particular environmental constraints. If components other than water are present in the system, it may be necessary to remove those components or sufficiently dilute them by introducing additional amounts of water into the system. The reason for this is that certain components may have an adverse effect upon the second conversion step described in detail below.

The second conversion step involves the conversion of all isoflavone glucones in the mixture including isoflavone glucones initially present in the vegetable protein material prior to the first conversion step as well as isoflavone glucones produced in the first conversion step, to isoflavone aglucones. The conversion is effected by contacting the isoflavone glucones in the mixture with an enzyme capable of cleaving isoflavone glucoside bonds at a temperature and a pH and for a time period sufficient to effect the conversion.

This conversion is primarily dependent upon the concentration of enzymes present in the mixture, and their characteristics. These enzymes may be naturally present in the vegetable protein material, may be present from microbial growth in that material, or may be added to the vegetable protein material. Enzyme that is naturally present in the vegetable or soybean material, or that is present from microbial growth, is referred to herein as "residual enzyme". Enzyme which is added is referred to herein as "supplemental enzyme". Generally, if the concentration of residual enzyme in the vegetable protein material is insufficient to convert a majority, and preferably substantially all isoflavones in glucone form to aglucone form, then supplemental enzyme should be added.

The amount of enzyme necessary to perform the conversion in the second step depends upon a variety of factors including the types of enzymes present, distribution of enzyme concentrations, pH of the system, activities of enzymes present, and temperature of the system. The preferred amount of enzyme added, if any, is typically an amount such that the total concentration of enzyme present is from about 0.1% to about 10% by weight of the vegetable protein material on a dry basis. Once sufficient concentrations of enzymes are present in the system, via residual enzymes, supplemental enzymes, or both, the isoflavone glucones are contacted with the enzymes at a temperature, pH, and for a time period sufficient to convert a majority, and preferably substantially all, of the isoflavone glucones in the mixture to the isoflavone aglucone form.

Preferred supplemental enzymes are selected based upon the pH of the mixture environment and comprise nearly all saccharidase enzymes, that is, enzymes capable of cleaving 1,4-glucoside bonds. Such enzymes can be derived from, for example, Aspergillus Niger, Aspergillus Oryzae, Kluyveromyces Lactis, and Kluyveromyces Fragilis. Preferred supplemental enzymes are commercially available alpha- and beta-galactosidase enzymes, and pectinase enzymes. Particularly preferred commercially available enzymes are: BIOPECTINASE 100L (which is preferably utilized at a pH range of from about 3 to about 6), BIOPECTINASE 300L (optimum pH range from about 3 to about 6), BIOPECTINASE OK 70L (optimum pH range from about 3 to about 6), BIOLACTASE 30,000 (optimum pH range from about 3 to about 6) Neutral Lactase (optimum pH range from about 6 to about 8), all of which are available from Quest International, 1833 57th Street, Post Office Box 3917, Sarasota, Fla. 34243. Also especially preferred are Lactase F (which is preferably utilized at a pH range of from about 4 to about 6), and LACTASE 50,000 (optimum pH range from about 4 to about 6), both available from Amano International Enzyme Co., Inc., Post Office Box 1000, Troy, Va. 22974. Other particularly preferred enzymes include LACTOZYME 3000L (which preferably is utilized at a pH range of from about 6 to about 8), and ALPHA-Gal 600L (which preferably is utilized at a pH of from about 4 to about 6.5), available from Novo Nordisk Bioindustrials, Inc., 33 Turner Road, Danbury, Conn. 06813; MAXILACT L2000 (which is preferably utilized at a pH range of from about 4 to about 6), available from Gist Brocades Food Ingredients, Inc., King of Prussia, Pa., 19406; NEUTRAL LACTASE (which is preferably utilized at a pH range of from about 6 to about 8), available from Pfizer Food Science Group, 205 East 42nd Street, New York, N. Y. 10017; and ENZECO FUNGAL LACTASE CONCENTRATE (which is preferably utilized at a pH range of from about 4 to about 6), available from Enzyme Development Corporation, 2 Penn Plaza, Suite 2439, New York, N.Y. 10121.

It has also been discovered that certain gluco-amylase enzymes can be utilized instead of, or in addition to, the previously noted enzymes. An example of a suitable gluco-amylase is G-ZYME G990 (which preferably is used as a pH range of from about 4 to about 6), available from Enzyme Development Corporation.

Prior to initiating the second conversion step, it is not necessary to transfer the system produced from the first conversion step into a different container or reaction vessel. Moreover, it is not necessary to employ laborious, time consuming, or costly separating or processing operations upon the reaction mixture or any portion thereof. Instead, the product from the first conversation step may be used directly as the feed material for the second conversion step. The only parameters that need be adjusted or monitored are pH and temperature.

The second conversion step may be effected at pH of about 3 to about 9. The preferred pH range for the second conversion step is from about 3 to about 8. The pH that is utilized depends primarily upon the type of enzyme used and so should be selected accordingly. The pH may be adjusted, in most instances reduced from the relatively high or basic pH of the first step, by a variety of methods such as by the addition of one or more suitable acids such as acetic acid, sulfuric acid, phosphoric acid, hydrochloric acid or any other suitable reagent. It is contemplated that in most instances it is preferable to utilize a foodgrade acidic reagent or acid.

The second conversion step may be performed at a temperature of about 5° C. to about 75° C. The preferred temperature for the second conversion step is from about 5° C. to about 60° C. The most preferred temperature is about 35° C. to about 55° C. It is preferred that the reaction system be maintained at a relatively constant temperature throughout the entire period for the conversion from isoflavone glucones to isoflavone aglucones. However, it is envisioned that in some instances it might be desirable to increase, decrease, or otherwise vary the temperature over the time period for the second conversion step.

The time required for the second conversion step depends primarily upon various enzyme-related factors, and the temperature and pH of the system. In most instances it is possible to achieve substantial conversion within 24 hours. The time required to effect the second conversion step can be remarkably reduced by the addition of a supplemental enzyme, and may be as short as about 1 hour to about 3 hours.

The second conversion step can convert at least a majority of the isoflavone glucones in the mixture to isoflavone aglucones. The extent of conversion of isoflavone glucones to isoflavone aglucones during the second step is typically from at least about 80% up to 100%, and preferably from about 90% to about 100%. By use of the preferred reaction parameters previously described, it is possible to achieve conversions of about 95% or higher. Such high rates of conversion on a dependable basis are remarkable, and are desirable for commercial applications.

Upon completion of the second conversion step, the relatively insoluble isoflavone aglucones are removed from the system, preferably by centrifugation or filtration. Once removed, the aglucones may be further separated from any particulate or other solid material by extraction with a suitable solvent. Examples of such solvents include but are not limited to acetone and/or an alcohol such as ethanol. It is also envisioned that one or more flocculating agents could be added to the system or mixture before, during, or after the second conversion step to facilitate precipitation of isoflavone aglucones.

The following examples describe specific but nonlimiting embodiments of the present invention.

EXPERIMENTAL

The present invention is illustrated in more detail by the following examples using a soy material as the vegetable material. The examples are intended to be illustrative, and should not be interpreted as limiting or otherwise restricting the scope of the invention in any way.

Vegetable protein materials such as soy protein isolates, concentrates, or flours include the genistein, daidzein, and glycitein "families" of isoflavones having corresponding conjugate, glucone, and aglucone members, where the genistein family contains the conjugates 6"-OMal genistin, and 6"-OAc genistin, the glucone genistin, and the aglucone genistein; the daidzein family contains the conjugates 6"-OMal daidzin and 6"-OAc daidzin, the glucone daidzin, and the aglucone daidzein; and the glycitein family contains the conjugate 6"-OMal glycitin, the glucone glycitin, and the aglucone glycitein. In the following examples the relative concentrations of the isoflavones are measured as a percentage of a family of isoflavones. For example, in the genistein family: %6"-OMal genistin +%6"-OAc genistin +% genistin +% genistein =100%. The extent of conversion of conjugates to glucones, and glucones to aglucones can be determined by comparing the percentages of each type of compound in an isoflavone family.

EXAMPLE 1

Samples containing vegetable protein material were prepared by forming aqueous mixtures of primary soybean whey. In a first series of experiments, the first conversion step was performed by adjusting the pH of all samples to 9.0, and incubating for 3.5 hours at 72.5° C. After cooling the samples and adjusting their pH to 7.0, three groups of samples were formed prior to performing the second conversion step. In the first group, the pH was left at a value of 7.0. For the second group, the pH was adjusted to 8.0. And in the third group, the pH was adjusted to 9.0. Each group was then split into two classes in which a second incubation occurred at either 45° C. or 55° C. All samples were incubated for 24 hours with periodic analysis conducted at 0, 2, 4, 6, and 24 hours.

Table 1 set forth below indicates the percent conversion of isoflavone conjugates to isoflavone aglucones in soybean material by application of the process herein.

TABLE 1

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGE | | | | | | |
| pH 7.0 @ 45° C. | | | | | | | | | | | |
| t = 0 | 86 | 5 | 0 | 9 | 79 | 4 | 0 | 18 | 100 | 0 | 0 |
| t = 2 hrs | 85 | 6 | 0 | 9 | 78 | 4 | 0 | 18 | 100 | 0 | 0 |
| t = 4 hrs | 86 | 5 | 0 | 9 | 78 | 4 | 0 | 18 | 100 | 0 | 0 |
| t = 6 hrs | 87 | 5 | 0 | 9 | 79 | 3 | 0 | 18 | 100 | 0 | 0 |
| t = 24 hrs | 0 | 1 | 0 | 99 | 0 | 2 | 0 | 98 | 0 | 0 | 100 |
| pH 8.0 @ 45° C. | | | | | | | | | | | |
| t = 0 | 86 | 5 | 0 | 9 | 79 | 4 | 0 | 18 | 100 | 0 | 0 |
| t = 2 hrs | 87 | 4 | 0 | 9 | 79 | 3 | 0 | 18 | 100 | 0 | 0 |
| t = 4 hrs | 88 | 4 | 0 | 9 | 79 | 3 | 0 | 15 | 100 | 0 | 0 |
| t = 6 hrs | 89 | 3 | 0 | 8 | 80 | 2 | 0 | 18 | 100 | 0 | 0 |
| t = 24 hrs | 0 | 3 | 0 | 97 | 0 | 3 | 0 | 97 | 0 | 0 | 100 |
| pH 9.0 @ 45° C. | | | | | | | | | | | |
| t = 0 | 86 | 5 | 0 | 9 | 79 | 4 | 0 | 18 | 100 | 0 | 0 |
| t = 2 hrs | 89 | 2 | 0 | 9 | 81 | 1 | 0 | 18 | 100 | 0 | 0 |
| t = 4 hrs | 92 | 1 | 0 | 8 | 82 | 0 | 0 | 18 | 100 | 0 | 0 |
| t = 6 hrs | 93 | 0 | 0 | 7 | 82 | 0 | 0 | 18 | 100 | 0 | 0 |
| t = 24 hrs | 0 | 0 | 0 | 100 | 0 | 0 | 0 | 100 | 0 | 0 | 100 |
| pH 7.0 @ 55° C. | | | | | | | | | | | |
| t = 0 | 86 | 5 | 0 | 9 | 79 | 4 | 0 | 18 | 100 | 0 | 0 |
| t = 2 hrs | 86 | 5 | 0 | 9 | 78 | 4 | 0 | 18 | 100 | 0 | 0 |
| t = 4 hrs | 87 | 5 | 0 | 8 | 79 | 3 | 0 | 18 | 100 | 0 | 0 |
| t = 6 hrs | 88 | 4 | 0 | 8 | 80 | 3 | 0 | 18 | 100 | 0 | 0 |
| t = 24 hrs | 0 | 1 | 0 | 99 | 0 | 2 | 0 | 98 | 0 | 0 | 100 |
| pH 8.0 @ 55° C. | | | | | | | | | | | |
| t = 0 | 86 | 5 | 0 | 9 | 79 | 4 | 0 | 18 | 100 | 0 | 0 |
| t = 2 hrs | 87 | 4 | 0 | 9 | 79 | 3 | 0 | 18 | 100 | 0 | 0 |
| t = 4 hrs | 89 | 3 | 0 | 8 | 80 | 2 | 0 | 18 | 100 | 0 | 0 |
| t = 6 hrs | 91 | 2 | 0 | 7 | 81 | 1 | 0 | 17 | 100 | 0 | 0 |

TABLE 1-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| t = 24 hrs | 0 | 0 | 0 | 100 | 0 | 1 | 0 | 99 | 0 | 0 | 100 |
| pH 9.0 @ 55° C. | | | | | | | | | | | |
| t = 0 | 86 | 5 | 0 | 9 | 79 | 4 | 0 | 18 | 100 | 0 | 0 |
| t = 2 hrs | 91 | 1 | 0 | 8 | 82 | 0 | 0 | 17 | 100 | 0 | 0 |
| t = 4 hrs | 93 | 0 | 0 | 7 | 83 | 0 | 0 | 17 | 100 | 0 | 0 |
| t = 6 hrs | 95 | 0 | 0 | 5 | 83 | 0 | 0 | 17 | 100 | 0 | 0 |
| t = 24 hrs | 0 | 0 | 0 | 100 | 0 | 0 | 0 | 100 | 0 | 0 | 100 |

The complete or substantially-completed conversion of isoflavone conjugates to aglucones occurred between 6 and 24 hours of incubation at all pHs and at both 45° C. and 55° C. Although not wishing to be bound to any particular theory, it is believed that the lag period occurring prior to conversion to the aglucone forms and observable from the above data, results from the time period for biosynthesis to occur, that is the formation of residual soy or microbial enzyme. The lag period may also result from the production of a second participant in the reaction, depletion of another enzyme substrate, and/or binding of the enzyme and/or substrate.

EXAMPLE 2

In a second series of experiments, the first conversion step was performed by adjusting the pH of all samples to 11.0 and heating to 50° C. for 1 hour. The samples were then cooled and their pH was adjusted to either 4.0 or 4.5. In the first group, an effective amount of BIOPECTINASE 100L was added, and in the second group, an effective amount of LACTASE F was added. The samples were then incubated for 1 hour at either 50° C. for 60° C.

Table II set forth below indicates the percent conversion of isoflavone conjugates to isoflavone aglucones in soybean material by application of the process described herein.

TABLE II

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| First Step Conversion | | | | | | | | | | | |
| Before: | 25.9 | 61.6 | 0 | 12.5 | 28.4 | 58.2 | 2.9 | 10.5 | 37.9 | 55.4 | 6.7 |
| After: | 89.5 | 0.0 | 0 | 10.5 | 89.7 | 0.0 | 0.0 | 10.3 | 100.0 | 0.0 | 0.0 |
| Second Step Conversion | | | | | | | | | | | |
| pH 4.5, 50° C., 1 hr | | | | | | | | | | | |
| Percent BIOPECTINASE 100L (solids basis) | | | | | | | | | | | |
| 5.3 | 9.9 | 0 | 0 | 90.1 | 7.9 | 0 | 0 | 92.1 | 74.8 | 0 | 25.2 |
| 4.4 | 20.4 | 0 | 0 | 79.6 | 18.6 | 0 | 0 | 81.4 | 75.2 | 0 | 24.8 |
| 2.2 | 43.1 | 0 | 0 | 56.9 | 42.2 | 0 | 0 | 57.8 | 77.8 | 0 | 22.2 |
| 1.1 | 62.4 | 0 | 0 | 37.6 | 62.0 | 0 | 0 | 38.0 | 100.0 | 0 | 0.0 |
| 0.5 | 75.4 | 0 | 0 | 24.6 | 75.1 | 0 | 0 | 24.9 | 100.0 | 0 | 0.0 |
| Percent LACTASE F (solids basis) | | | | | | | | | | | |
| 11.1 | 0.0 | 0 | 0 | 100.0 | 0 | 0.0 | 0 | 100.0 | 0.0 | 0 | 100.0 |
| 8.9 | 0.0 | 0 | 0 | 100.0 | 0 | 0.0 | 0 | 100.0 | 0.0 | 0 | 100.0 |
| 4.4 | 0.0 | 0 | 0 | 100.0 | 0 | 2.4 | 0 | 97.6 | 0.0 | 0 | 100.0 |
| 2.2 | 0.0 | 0 | 0 | 100.0 | 0 | 2.1 | 0 | 97.9 | 0.0 | 0 | 100.0 |
| 1.1 | 0.0 | 0 | 0 | 100.0 | 0 | 2.1 | 0 | 97.9 | 0.0 | 0 | 100.0 |
| 0.6 | 4.2 | 0 | 0 | 95.8 | 0 | 2.2 | 0 | 97.8 | 15.9 | 0 | 84.1 |
| pH 4.5, 60° C., 1 hr | | | | | | | | | | | |
| Percent BIOPECTINASE 100L (solids basis) | | | | | | | | | | | |
| 5.3 | 5.5 | 0 | 0 | 94.5 | 5.0 | 0 | 0 | 95.0 | 71.0 | 0 | 29.0 |
| 4.4 | 12.9 | 0 | 0 | 87.1 | 12.5 | 0 | 0 | 87.5 | 100.0 | 0 | 0.0 |
| 2.2 | 70.9 | 0 | 0 | 29.1 | 34.6 | 0 | 0 | 65.4 | 75.5 | 0 | 24.5 |
| 1.1 | 55.0 | 0 | 0 | 45.0 | 55.9 | 0 | 0 | 44.1 | 78.5 | 0 | 21.5 |
| 0.6 | 70.9 | 0 | 0 | 29.1 | 72.2 | 0 | 0 | 27.8 | 100.0 | 0 | 0.0 |

TABLE II-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| Percent LACTASE F (solids basis) | | | | | | | | | | | |
| 11.1 | 0.0 | 0 | 0 | 100.0 | 0.0 | 0.0 | 0 | 100.0 | 0 | 0 | 100.0 |
| 8.9 | 0.0 | 0 | 0 | 100.0 | 0.0 | 2.3 | 0 | 97.7 | 0 | 0 | 100.0 |
| 4.4 | 0.0 | 0 | 0 | 100.0 | 0.0 | 2.2 | 0 | 97.8 | 0 | 0 | 100.0 |
| 2.2 | 0.0 | 0 | 0 | 100.0 | 0.0 | 2.1 | 0 | 97.9 | 0 | 0 | 100.0 |
| 1.1 | 0.0 | 0 | 0 | 100.0 | 0.0 | 2.1 | 0 | 97.9 | 0 | 0 | 100.0 |
| 0.6 | 5.2 | 0 | 0 | 94.8 | 4.0 | 2.2 | 0 | 93.8 | 29 | 0 | 71.0 |
| pH 4.0, 50° C., 1 hr | | | | | | | | | | | |
| Percent BIOPECTINASE 100L (solids basis) | | | | | | | | | | | |
| 5.3 | 13.4 | 0 | 0 | 86.6 | 12.5 | 0 | 0 | 87.5 | 75.8 | 0 | 24.2 |
| 4.4 | 23.0 | 0 | 0 | 77.0 | 22.5 | 0 | 0 | 77.5 | 76.6 | 0 | 23.4 |
| 2.1 | 65.3 | 0 | 0 | 34.7 | 66.0 | 0 | 0 | 34.0 | 100.0 | 0 | 0.0 |
| 1.1 | 66.4 | 0 | 0 | 33.6 | 67.0 | 0 | 0 | 33.0 | 100.0 | 0 | 0.0 |
| 0.5 | 77.9 | 0 | 0 | 22.1 | 77.7 | 0 | 0 | 23.3 | 100.0 | 0 | 0.0 |
| Percent LACTASE F (solids basis) | | | | | | | | | | | |
| 4.4 | 0 | 0 | 0 | 100.0 | 0 | 2.2 | 0 | 97.8 | 0.0 | 0 | 100.0 |
| 2.2 | 0 | 0 | 0 | 100.0 | 0 | 2.1 | 0 | 97.9 | 0.0 | 0 | 100.0 |
| 1.1 | 0 | 0 | 0 | 100.0 | 0 | 2.2 | 0 | 97.8 | 24.9 | 0 | 75.1 |
| 0.6 | 0 | 0 | 0 | 100.0 | 0 | 2.4 | 0 | 97.6 | 44.2 | 0 | 55.8 |
| pH 4.0, 60° C., 1 hr | | | | | | | | | | | |
| Percent BIOPECTINASE 100L (solids basis) | | | | | | | | | | | |
| 5.3 | 10.1 | 0 | 0 | 89.9 | 10.4 | 0 | 0 | 89.6 | 72.8 | 0 | 27.2 |
| 4.4 | 21.4 | 0 | 0 | 78.6 | 22.6 | 0 | 0 | 77.4 | 74.2 | 0 | 25.8 |
| 2.2 | 45.1 | 0 | 0 | 54.9 | 46.7 | 0 | 0 | 53.3 | 77.9 | 0 | 22.1 |
| 1.1 | 65.6 | 0 | 0 | 34.4 | 67.2 | 0 | 0 | 32.8 | 100.0 | 0 | 0.0 |
| 0.5 | 73.5 | 0 | 0 | 26.5 | 75.1 | 0 | 0 | 25.5 | 100.0 | 0 | 0.0 |
| Percent LACTASE (solids basis) | | | | | | | | | | | |
| 4.4 | 0.0 | 0 | 0 | 100.0 | 0.0 | 2.2 | 0 | 97.8 | 30.9 | 0 | 69.2 |
| 2.2 | 2.1 | 0 | 0 | 97.9 | 0.0 | 2.1 | 0 | 97.9 | 54.0 | 0 | 46.0 |
| 1.1 | 14.6 | 0 | 0 | 85.4 | 19.4 | 0.0 | 0 | 80.6 | 67.1 | 0 | 32.9 |
| 0.6 | 41.3 | 0 | 0 | 58.7 | 47.9 | 0.0 | 0 | 52.1 | 74.3 | 0 | 25.7 |

EXAMPLE 3

In a third series of experiments, the first conversion step was performed by adjusting the pH of all samples to 11.0 and heating to 20° C. for 1 hour. The samples were then cooled and three groups were formed according to adjustment of pH to values of 4.0, 4.5, and 5.0. Biopectinase 100L was added to each sample to a concentration of 0.04g BIOPECTINASE per 100g primary whey. All samples were then incubated for 1 hour at 50° C.

Table III presented below, sets forth the percent conversion of isoflavone conjugates to isoflavone aglucones in soybean material by application of the process described herein.

TABLE III

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| First Step Conversion | | | | | | | | | | | |
| Before: | 18.6 | 32.8 | 0 | 48.5 | 32.2 | 32.8 | 0 | 34.9 | 33.6 | 28.0 | 38.4 |
| After: | 52.3 | 2.5 | 0 | 45.2 | 63.5 | 1.8 | 0 | 34.7 | 60.1 | 0.0 | 39.9 |

TABLE III-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| Second Step Conversion | | | | | | | | | | | |
| pH 5.0 | | | | | | | | | | | |
| t = 0 hrs | 51.0 | 2.5 | 0 | 46.5 | 62.2 | 1.8 | 0 | 36.0 | 59.1 | 0 | 40.8 |
| t = 0.5 hrs | 39.4 | 2.5 | 0 | 58.1 | 47.9 | 1.8 | 0 | 50.3 | 57.1 | 0 | 42.9 |
| t = 1.0 hrs | 30.6 | 2.4 | 0 | 66.9 | 37.6 | 1.8 | 0 | 60.6 | 55.6 | 0 | 44.4 |
| t = 1.5 hrs | 23.0 | 2.4 | 0 | 74.6 | 28.6 | 1.6 | 0 | 69.8 | 54.9 | 0 | 45.1 |
| t = 2.0 hrs | 18.2 | 2.2 | 0 | 79.6 | 22.5 | 1.6 | 0 | 75.9 | 53.4 | 0 | 46.6 |
| t = 3.0 hrs | 11.9 | 2.1 | 0 | 86.0 | 14.6 | 1.6 | 0 | 83.8 | 51.4 | 0 | 58.6 |
| pH 4.5 | | | | | | | | | | | |
| t = 0 hrs | 50.4 | 2.5 | 0 | 47.1 | 61.1 | 1.8 | 0 | 37.1 | 60.1 | 0 | 39.9 |
| t = 0.5 hrs | 35.0 | 2.4 | 0 | 62.6 | 43.6 | 1.6 | 0 | 54.8 | 56.5 | 0 | 43.5 |
| t = 1.0 hrs | 24.5 | 2.3 | 0 | 72.9 | 31.1 | 1.8 | 0 | 67.2 | 54.3 | 0 | 54.7 |
| t = 1.5 hrs | 16.3 | 2.1 | 0 | 81.6 | 20.2 | 1.4 | 0 | 78.4 | 53.3 | 0 | 46.7 |
| t = 2.0 hrs | 12.1 | 2.1 | 0 | 85.8 | 15.4 | 1.4 | 0 | 83.1 | 50.9 | 0 | 49.1 |
| t = 3.0 hrs | 6.7 | 1.8 | 0 | 91.5 | 8.5 | 1.3 | 0 | 90.2 | 0.0 | 0 | 100.0 |
| pH 4.0 | | | | | | | | | | | |
| t = 0 hrs | 50.0 | 2.5 | 0 | 47.5 | 60.1 | 1.9 | 0 | 38.1 | 59.5 | 0 | 40.5 |
| t = 0.5 hrs | 34.4 | 2.4 | 0 | 63.3 | 42.2 | 1.8 | 0 | 56.1 | 55.0 | 0 | 45.0 |
| t = 1.0 hrs | 24.3 | 2.3 | 0 | 73.4 | 30.0 | 1.6 | 0 | 68.4 | 55.0 | 0 | 45.0 |
| t = 1.5 hrs | 16.3 | 2.1 | 0 | 81.6 | 20.2 | 1.4 | 0 | 78.4 | 53.3 | 0 | 46.7 |
| t = 2.0 hrs | 12.1 | 2.1 | 0 | 85.8 | 15.4 | 1.6 | 0 | 83.1 | 51.9 | 0 | 48.1 |
| t = 3.0 hrs | 6.4 | 1.7 | 0 | 91.9 | 7.5 | 1.2 | 0 | 91.3 | 49.3 | 0 | 50.7 |

EXAMPLE 4

In a fourth series of experiments, the first conversion step was performed by adjusting the pH of all samples to 8.0 and maintaining the temperature at 72.5° C. for 24 hours. Samples were withdrawn over the course of the 24 hour period.

Table IV presented below, sets forth the percent conversion of isoflavone conjugates to isoflavone glucones in soybean material by application of the first step of the process described herein.

TABLE IV

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| pH 8.0 | | | | | | | | | | | |
| t = 0 hrs | 27 | 52 | 0 | 21 | 28 | 52 | 2 | 18 | 41 | 43 | 16 |
| t = 2 hrs | 53 | 30 | 0 | 17 | 52 | 29 | 1 | 18 | 58 | 26 | 16 |
| t = 4 hrs | 66 | 19 | 0 | 15 | 64 | 17 | 1 | 18 | 70 | 15 | 15 |
| t = 6 hrs | 73 | 13 | 0 | 14 | 71 | 11 | 1 | 17 | 72 | 11 | 17 |
| t = 9 hrs | 81 | 7 | 0 | 12 | 77 | 6 | 0 | 17 | 78 | 6 | 16 |
| t = 24 hrs | 79 | 1 | 0 | 20 | 79 | 0 | 0 | 21 | 80 | 0 | 20 |

EXAMPLE 5

In a fifth series of experiments, the second conversion step was performed by utilizing a variety of different commercially available beta-galactosidase enzymes. Primary whey obtained from soybean material was slurried with water to a solids content of 5%. The pH was adjusted to 11 and the temperature maintained at 25° C. for 45 minutes to convert isoflavone conjugates to isoflavone glucones. Samples were then formed to determine conversion by each enzyme at concentrations of 2% and 10%, a temperature of 50° C., and at pH values of 4.5 and 7.0 the extent of conversion was measured at t=0, 1, and 4 hours.

Table V presented below, sets forth the percent conversion and resulting distribution of isoflavones.

TABLE V

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| 2% NOVO LACTOZYME 3000L | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 78 | 8 | 0 | 14 | 80 | 7 | 0 | 13 | 86 | 0 | 14 |
| t = 4 hr | 77 | 8 | 0 | 15 | 80 | 7 | 0 | 13 | 84 | 0 | 16 |
| pH 7.0 | | | | | | | | | | | |
| t = 0 hr | 78 | 7 | 0 | 15 | 77 | 7 | 0 | 16 | 75 | 6 | 19 |
| t = 1 hr | 72 | 8 | 0 | 20 | 77 | 7 | 0 | 16 | 72 | 0 | 28 |
| t = 4 hr | 68 | 8 | 0 | 24 | 74 | 7 | 0 | 19 | 61 | 0 | 39 |
| 10% NOVO LACTOZYME 3000L | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 78 | 8 | 0 | 14 | 80 | 7 | 0 | 13 | 84 | 0 | 16 |
| t = 4 hr | 78 | 8 | 0 | 14 | 80 | 7 | 0 | 13 | 82 | 0 | 18 |
| pH 7.0 | | | | | | | | | | | |
| t = 0 hr | 78 | 7 | 0 | 15 | 77 | 7 | 0 | 16 | 75 | 6 | 19 |
| t = 1 hr | 53 | 9 | 0 | 38 | 66 | 8 | 0 | 26 | 25 | 0 | 75 |
| t = 4 hr | 32 | 10 | 0 | 58 | 50 | 8 | 0 | 42 | 0 | 0 | 100 |
| 2% MAXILACT L2000 | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 78 | 7 | 0 | 15 | 77 | 7 | 0 | 16 | 75 | 6 | 19 |
| t = 4 hr | 76 | 7 | 0 | 17 | 76 | 7 | 0 | 17 | 73 | 6 | 21 |
| pH 7.0 | | | | | | | | | | | |
| t = 0 hr | 78 | 7 | 0 | 15 | 77 | 7 | 0 | 16 | 75 | 6 | 19 |
| t = 1 hr | 71 | 7 | 0 | 22 | 73 | 6 | 0 | 21 | 56 | 7 | 37 |
| t = 4 hr | 65 | 7 | 0 | 28 | 69 | 5 | 0 | 26 | 52 | 0 | 48 |
| 10% MAXILACT L2000 | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 78 | 7 | 0 | 15 | 78 | 6 | 0 | 16 | 75 | 6 | 19 |
| t = 4 hr | 77 | 6 | 0 | 17 | 77 | 6 | 0 | 17 | 77 | 0 | 23 |
| pH 7.0 | | | | | | | | | | | |
| t = 0 hr | 78 | 7 | 0 | 15 | 77 | 7 | 0 | 16 | 75 | 6 | 19 |
| t = 1 hr | 49 | 7 | 0 | 44 | 59 | 5 | 0 | 36 | 17 | 7 | 76 |
| t = 4 hr | 25 | 8 | 0 | 67 | 39 | 6 | 0 | 55 | 0 | 0 | 100 |
| 2% PFIZER NEUTRAL LACTASE | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 77 | 7 | 0 | 16 | 77 | 6 | 0 | 17 | 73 | 7 | 20 |
| t = 4 hr | 77 | 7 | 0 | 16 | 77 | 6 | 0 | 17 | 76 | 0 | 24 |
| pH 7.0 | | | | | | | | | | | |
| t = 0 hr | 78 | 7 | 0 | 15 | 77 | 7 | 0 | 16 | 75 | 6 | 19 |
| t = 1 hr | 70 | 7 | 0 | 23 | 72 | 5 | 0 | 23 | 70 | 6 | 24 |
| t = 4 hr | 55 | 7 | 0 | 38 | 60 | 6 | 0 | 34 | 66 | 0 | 34 |
| 10% Pfizer Neutral Lactose | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 78 | 6 | 0 | 16 | 78 | 5 | 0 | 17 | 73 | 7 | 20 |
| t = 4 hr | 78 | 6 | 0 | 16 | 77 | 6 | 0 | 17 | 76 | 0 | 24 |
| pH 7.0 | | | | | | | | | | | |
| t = 0 hr | 78 | 7 | 0 | 15 | 77 | 7 | 0 | 16 | 75 | 6 | 19 |
| t = 1 hr | 35 | 8 | 0 | 57 | 46 | 6 | 0 | 48 | 51 | 0 | 49 |
| t = 4 hr | 2 | 8 | 0 | 90 | 4 | 6 | 0 | 90 | 0 | 0 | 100 |

TABLE V-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| 2% QUEST BIOLACTASE 30,000 | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 0 | 6 | 0 | 94 | 0 | 6 | 0 | 94 | 0 | 0 | 100 |
| t = 4 hr | 0 | 4 | 0 | 96 | 0 | 5 | 0 | 95 | 0 | 0 | 100 |
| pH 7.0 | | | | | | | | | | | |
| t = 0 hr | 78 | 7 | 0 | 15 | 77 | 7 | 0 | 16 | 75 | 6 | 19 |
| t = 1 hr | 2 | 7 | 0 | 91 | 3 | 7 | 0 | 90 | 29 | 0 | 71 |
| t = 4 hr | 0 | 7 | 0 | 93 | 0 | 6 | 0 | 94 | 0 | 0 | 100 |
| 10% QUEST BIOLACTASE 30,000 | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 0 | 4 | 0 | 96 | 0 | 4 | 0 | 96 | 0 | 0 | 100 |
| t = 4 hr | 0 | 2 | 0 | 98 | 0 | 3 | 0 | 97 | 0 | 0 | 100 |
| pH 7.0 | | | | | | | | | | | |
| t = 0 hr | 78 | 7 | 0 | 15 | 77 | 7 | 0 | 16 | 75 | 6 | 19 |
| t = 1 hr | 0 | 7 | 0 | 93 | 0 | 7 | 0 | 93 | 0 | 0 | 100 |
| t = 4 hr | 0 | 7 | 0 | 93 | 0 | 6 | 0 | 94 | 0 | 0 | 100 |
| 2% QUEST NEUTRAL LACTASE | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 73 | 6 | 0 | 21 | 76 | 5 | 0 | 19 | 79 | 0 | 21 |
| t = 4 hr | 73 | 6 | 0 | 21 | 76 | 5 | 0 | 19 | 76 | 0 | 24 |
| pH 7.0 | | | | | | | | | | | |
| t = 0 hr | 78 | 7 | 0 | 15 | 77 | 7 | 0 | 16 | 75 | 6 | 19 |
| t = 1 hr | 2 | 7 | 0 | 91 | 7 | 4 | 0 | 89 | 15 | 0 | 85 |
| t = 4 hr | 0 | 7 | 0 | 93 | 0 | 4 | 0 | 96 | 0 | 0 | 100 |
| 10% QUEST NEUTRAL LACTASE | | | | | | | | | | | |
| pH 4.5 | | | | | | | | | | | |
| t = 0 hr | 78 | 7 | 0 | 15 | 77 | 7 | 0 | 16 | 75 | 6 | 19 |
| t = 1 hr | 73 | 6 | 0 | 21 | 76 | 5 | 0 | 19 | 79 | 0 | 21 |
| t = 4 hr | 72 | 6 | 0 | 22 | 75 | 5 | 0 | 20 | 77 | 0 | 23 |
| pH 7.0 | | | | | | | | | | | |
| t = 0 hr | 78 | 7 | 0 | 15 | 77 | 7 | 0 | 16 | 75 | 6 | 19 |
| t = 1 hr | 0 | 7 | 0 | 93 | 0 | 4 | 0 | 96 | 0 | 0 | 100 |
| t = 4 hr | 0 | 7 | 0 | 93 | 0 | 4 | 0 | 96 | 0 | 0 | 100 |

EXAMPLE 6

In a sixth series of experiments, the second conversion step was performed upon material produced from the first step conversion in the previously described fifth series of experiments. The second conversion step was performed by utilizing BIOPECTINASE 100L and LACTASE F at 50° C. and at a pH of 3.0, in concentrations of 5% and 10%.

Table VI set forth below provides the percent conversion obtained by utilizing those enzymes.

TABLE VI

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| 5% BIOPECTINASE 100L | | | | | | | | | | | |
| t = 0 hr | 78 | 7 | 0 | 15 | 77 | 7 | 0 | 16 | 75 | 6 | 19 |
| t = 1 hr | 30 | 5 | 0 | 65 | 30 | 5 | 0 | 65 | 67 | 0 | 33 |
| t = 4 hr | 27 | 4 | 0 | 69 | 27 | 4 | 0 | 69 | 61 | 0 | 39 |

TABLE VI-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| t = 7 hr | 11 | 3 | 0 | 86 | 10 | 3 | 0 | 87 | 52 | 0 | 48 |
| 10% Biopectinase 100L | | | | | | | | | | | |
| t = 0 hr | 78 | 7 | 0 | 15 | 77 | 7 | 0 | 16 | 75 | 6 | 19 |
| t = 1 hr | 27 | 4 | 0 | 79 | 27 | 4 | 0 | 69 | 61 | 0 | 39 |
| t = 4 hr | 9 | 2 | 0 | 89 | 9 | 1 | 0 | 90 | 41 | 0 | 59 |
| t = 7 hr | 8 | 1 | 0 | 91 | 8 | 1 | 0 | 91 | 34 | 0 | 51 |
| 5% LACTASE F | | | | | | | | | | | |
| t = 0 hr | 78 | 7 | 0 | 15 | 77 | 7 | 0 | 16 | 75 | 6 | 19 |
| t = 1 hr | 68 | 7 | 0 | 25 | 71 | 6 | 0 | 23 | 80 | 0 | 20 |
| t = 4 hr | 68 | 6 | 0 | 26 | 71 | 6 | 0 | 23 | 80 | 0 | 20 |
| t = 7 hr | 68 | 6 | 0 | 26 | 71 | 6 | 0 | 23 | 79 | 0 | 21 |
| 10% LACTASE F | | | | | | | | | | | |
| t = 0 hr | 78 | 7 | 0 | 15 | 77 | 7 | 0 | 16 | 75 | 6 | 19 |
| t = 1 hr | 65 | 7 | 0 | 28 | 68 | 6 | 0 | 26 | 79 | 0 | 21 |
| t = 4 hr | 64 | 6 | 0 | 29 | 67 | 6 | 0 | 27 | 78 | 0 | 22 |
| t = 7 hr | 64 | 6 | 0 | 30 | 67 | 5 | 0 | 28 | 78 | 0 | 22 |

EXAMPLE 7

In another series of experiments, the first conversion step was performed by adjusting the pH of aqueous samples containing a 10% suspension of spray dried primary whey, to a value of 11, heating to 35° C., and holding for 30 minutes. The resulting glucoside-rich samples were then pH adjusted to a value of 4.5 and partitioned into 150 g samples. Three different commercially available enzymes were then added to the samples, ALPHA-GAL 600L, G-ZYME 990, and BIOLACTASE 30,000. To each sample, 0.15g of one enzyme type was added. The samples were then incubated at 50° C. for 4 hours. Measurements of the degree of conversion from isoflavone glucosides to isoflavone aglucones were taken from each incubating sample at 0, 1, 2, 3, and 4 hours after enzyme addition.

Table VII set forth below provides the percent conversion obtained by utilizing the particular enzymes.

TABLE VI

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| Glucoside-rich Primary Whey Starting Material | 83 | 0 | 0 | 17 | 83 | 0 | 0 | 40 | 81 | 5 | 13 |
| ALPHA-GAL 600L | | | | | | | | | | | |
| t = 0 hr | 66 | 1 | 0 | 33 | 63 | 0 | 0 | 37 | 80 | 0 | 20 |
| t = 1 hr | 4 | 0 | 0 | 96 | 2 | 0 | 0 | 98 | 23 | 0 | 77 |
| t = 2 hr | 1 | 0 | 0 | 99 | 0 | 0 | 0 | 100 | 10 | 14 | 76 |
| t = 3 hr | 0 | 0 | 0 | 100 | 0 | 0 | 0 | 100 | 6 | 0 | 94 |
| t = 4 hr | 0 | 0 | 0 | 100 | 0 | 0 | 0 | 100 | 8 | 14 | 78 |
| G ZYME 990 | | | | | | | | | | | |
| t = 0 hr | 63 | 1 | 0 | 37 | 60 | 0 | 0 | 40 | 79 | 0 | 21 |
| t = 1 hr | 49 | 1 | 0 | 51 | 41 | 0 | 0 | 59 | 82 | 0 | 18 |
| t = 2 hr | 30 | 1 | 0 | 69 | 21 | 0 | 0 | 79 | 79 | 0 | 21 |
| t = 3 hr | 18 | 0 | 0 | 82 | 11 | 0 | 0 | 89 | 69 | 11 | 19 |
| t = 4 hr | 11 | 1 | 0 | 88 | 5 | 0 | 0 | 95 | 67 | 12 | 21 |
| BIOLACTASE 30,000 | | | | | | | | | | | |
| t = 0 hr | 56 | 1 | 0 | 43 | 57 | 0 | 0 | 43 | 70 | 0 | 30 |
| t = 1 hr | 1 | 0 | 0 | 99 | 0 | 0 | 0 | 100 | 11 | 0 | 89 |
| t = 2 hr | 0 | 1 | 0 | 99 | 0 | 0 | 0 | 100 | 9 | 0 | 91 |
| t = 3 hr | 0 | 0 | 0 | 100 | 0 | 0 | 0 | 100 | 8 | 14 | 78 |
| t = 4 hr | 0 | 0 | 0 | 100 | 0 | 0 | 0 | 100 | 8 | 15 | 78 |

EXAMPLE 8

In an eighth series of experiments, isoflavone conjugates in a primary whey starting material were converted to isoflavone glucosides, by utilizing various combination of process parameters. First step conversion was achieved at a temperature of 121° C. and pH values of 6, 7.1, and 7.5; a temperature of 80° C. and pH values of 6, 7.1, and 7.5; and a temperature of 20° C. and pH values of 11.5, 12, 13, and 13.7. First step conversion was also achieved at relatively low temperatures such as 6° C. Table VIII set forth below provides the percent conversion achieved by the previously noted pH and temperature combinations. Conversions of isoflavone conjugates to their corresponding isoflavone glucoside form of 90% or more could be achieved by utilizing longer conversion times.

TABLE VIII

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| Starting Material Primary Whey | 17 | 62 | 0 | 21 | 10 | 68 | 2 | 20 | 29 | 46 | 25 |
| 121° C. (pH adjustment used Sodium hydroxide) | | | | | | | | | | | |
| pH 6.0 | 81 | 0 | 0 | 19 | 71 | 3 | 8 | 18 | 54 | 10 | 36 |
| pH 7.1 | 75 | 9 | 0 | 16 | 70 | 8 | 6 | 17 | 61 | 6 | 34 |
| pH 7.5 | 78 | 7 | 0 | 15 | 72 | 7 | 6 | 16 | 64 | 4 | 31 |
| 121° C. (pH adjustment used Calcium hydroxide) | | | | | | | | | | | |
| pH 6.0 | 72 | 13 | 0 | 15 | 64 | 12 | 7 | 16 | 56 | 9 | 35 |
| pH 7.1 | 77 | 8 | 0 | 15 | 71 | 7 | 6 | 17 | 62 | 5 | 33 |
| pH 7.5 | 84 | 4 | 0 | 12 | 77 | 3 | 4 | 15 | 72 | 0 | 28 |
| Samples held at 80° C. for 5 hrs (pH adjustment used Sodium hydroxide) | | | | | | | | | | | |
| pH 6.0 | 59 | 27 | 0 | 14 | 55 | 26 | 3 | 16 | 62 | 18 | 20 |
| pH 7.1 | 70 | 19 | 0 | 12 | 65 | 18 | 2 | 16 | 68 | 14 | 18 |
| pH 7.5 | 73 | 16 | 0 | 11 | 67 | 15 | 2 | 16 | 70 | 12 | 18 |
| Sample held at 80° C. for 5 hrs (pH adjustment used Calcium hydroxide) | | | | | | | | | | | |
| pH 6.0 | 61 | 26 | 0 | 13 | 56 | 26 | 3 | 15 | 61 | 18 | 21 |
| pH 7.1 | 72 | 17 | 0 | 12 | 65 | 16 | 2 | 16 | 67 | 13 | 20 |
| pH 7.5 | 80 | 10 | 0 | 10 | 73 | 9 | 2 | 16 | 74 | 8 | 18 |
| Sample held at 6° C. for 17.5 hr | | | | | | | | | | | |
| pH 9.5 | 73 | 14 | 0 | 13 | 72 | 13 | 0 | 15 | 91 | 0 | 9 |
| Samples held at 20° C. for 15 min | | | | | | | | | | | |
| pH 11.5 | 82 | 2 | 0 | 15 | 82 | 2 | 0 | 16 | 93 | 0 | 7 |
| pH 12.0 | 85 | 0 | 0 | 15 | 84 | 0 | 0 | 16 | 93 | 0 | 7 |
| pH 13.0 | 91 | 0 | 0 | 9 | 84 | 0 | 0 | 16 | 93 | 0 | 7 |
| pH 13.7 | 84 | 0 | 0 | 16 | 89 | 0 | 0 | 11 | 100 | 0 | 0 |

EXAMPLE 9

In another series of experiments, first step conversion of isoflavone conjugates to isoflavone glucosides in a primary whey mixture was carried out at temperatures of 2° C. and 6° C. at pH values of 11 and 12.3. The results of this testing are set forth in Table IX below.

TABLE IX

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| Conversion of conjugates to glucosides | | | | | | | | | | | |
| at 2° C. (ice bath) | | | | | | | | | | | |
| t = 0 | 17 | 62 | 0 | 21 | 10 | 68 | 3 | 20 | 29 | 46 | 25 |
| pH 11.0, t = 1 hr | 40 | 39 | 0 | 21 | 40 | 38 | 4 | 17 | 15 | 73 | 12 |
| pH 12.3, t = 1 hr | 81 | 0 | 0 | 19 | 83 | 0 | 0 | 17 | 100 | 0 | 0 |

TABLE IX-continued

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| at 6° C. (refrigerator) | | | | | | | | | | | |
| t = 0 | 17 | 62 | 0 | 21 | 10 | 68 | 3 | 20 | 29 | 46 | 25 |
| pH 11.0, t = 1 hr | 80 | 0 | 0 | 20 | 83 | 0 | 0 | 17 | 100 | 0 | 0 |
| pH 12.3, t = 1 hr | 81 | 0 | 0 | 19 | 77 | 0 | 0 | 23 | 100 | 0 | 0 |

EXAMPLE 10

In a tenth series of experiments, the second step conversion of isoflavone glucosides to isoflavone aglucones was performed at a temperature of 8° C. and pH values of 4.5 and 7, utilizing AMANO LACTASE 50,000 and QUEST NEUTRAL LACTASE enzymes, respectively. A glucoside-rich whey mixture was formed by subjecting a primary whey to the first step conversion at a pH of 11 and temperature of 35° C. for 45 minutes. After formation of the glucoside-rich mixture, the second step conversion was carried out.

Table X set forth below provides the percent conversion achieved by the noted pH and temperature combinations.

aglucones was performed at a temperature of 35° C. and pH values of 4.0 and 4.5. A first lot of samples of primary whey containing isoflavone conjugates was subjected to the first step conversion at a pH of 11 and temperature of 35° C. The resulting glucoside-rich mixture was then subjected to the second step conversion by utilizing 5% BIOPECTINASE 100L, pH of 4, and a temperature of 35° C. A second lot of samples of primary whey were converted to glucoside-rich samples as previously noted, after which 2% LACTASE F was utilized at a pH of 4 and a temperature of 35° C.

Table XI set forth below illustrates the percent conversion obtained.

TABLE X

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | PERCENTAGES | | | | | | | |
| Conversion of glucosides to aglucones with QUEST NEUTRAL LACTOSE pH 7.0, 8° C., t = 23 hrs | | | | | | | | | | | |
| t = 0 | 71 | 9 | 0 | 20 | 74 | 8 | 0 | 19 | 100 | 0 | 0 |
| t = 23 hrs 5% enzyme level | 12 | 10 | 0 | 78 | 26 | 9 | 0 | 65 | 49 | 0 | 51 |
| t = 23 hr, 10% enzyme level | 0 | 11 | 0 | 89 | 0 | 10 | 0 | 90 | 0 | 0 | 100 |
| Conversion of glucosides to aglucones with AMANO LACTASE 30,000 pH 4.5, 8° C., t = 23 hrs | | | | | | | | | | | |
| t = 0 | 71 | 9 | 0 | 20 | 74 | 8 | 400 | 19 | 100 | 0 | 0 |
| t = 23 hrs 5% enzyme level | 0 | 10 | 0 | 90 | 0 | 9 | 0 | 91 | 0 | 0 | 100 |
| t = 23 hr, 10% enzyme level | 0 | 10 | 0 | 90 | 0 | 9 | 0 | 91 | 0 | 0 | 100 |

EXAMPLE 11

In an eleventh series of experiments, the second conversion step in which isoflavone glucosides are converted to

TABLE XI

| Sample | GENI-STIN | 6"-OMAL-GENI-STIN | 6"-OAC-GENI-STIN | GENI-STEIN | DAIDZIN | 6"-OMAL-DAIDZIN | 6"-OAC-DAIDZIN | DAIDZEIN | GLYCITIN | 6"-OMAL-GLYCITIN | GLYCITEIN |
|---|---|---|---|---|---|---|---|---|---|---|---|
| | | | | | PERCENTAGES | | | | | | |
| Starting Material Primary Whey | 17 | 62 | 0 | 21 | 10 | 68 | 2 | 20 | 29 | 46 | 25 |
| Lot A (5% Biopectinase 100L)) | | | | | | | | | | | |
| Step 1.: Conversion of Conjugates to Glucosides, pH 11, 35° C. | | | | | | | | | | | |
| t = 45 min | 82 | 0 | 0 | 18 | 76 | 0 | 0 | 24 | 100 | 0 | 0 |
| t = 60 min | 84 | 0 | 0 | 16 | 77 | 0 | 0 | 23 | 100 | 0 | 0 |
| Step 2: Conversion of Glucosides to Aglucones pH 4.0, 35° C. | | | | | | | | | | | |
| t = 1 hr | 5 | 0 | 0 | 95 | 12 | 0 | 0 | 88 | 44 | 0 | 56 |
| t = 1.5 hr | 0 | 0 | 0 | 100 | 0 | 12 | 0 | 88 | 37 | 0 | 63 |
| t = 2.0 hr | 0 | 0 | 0 | 100 | 0 | 12 | 0 | 81 | 32 | 0 | 68 |
| Lot B (2% Lactase F) | | | | | | | | | | | |
| Step 1: Conversion of Conjugates to Glucosides pH 11, 35° C. | | | | | | | | | | | |
| t = 45 min | 83 | 0 | 0 | 17 | 77 | 0 | 0 | 23 | 100 | 0 | 0 |
| t = 60 min | 82 | 0 | 0 | 18 | 77 | 0 | 0 | 23 | 100 | 0 | 0 |
| Step 2: Conversion of Glucosides to Aglucones, pH 4.0, 35° C. | | | | | | | | | | | |
| t = 1 hr | 4 | 0 | 0 | 96 | 0 | 0 | 0 | 100 | 45 | 0 | 55 |
| t = 1.5 hr | 0 | 0 | 0 | 100 | 0 | 0 | 0 | 100 | 39 | 0 | 61 |
| t = 2.0 hr | 0 | 0 | 0 | 100 | 0 | 0 | 0 | 100 | 34 | 0 | 66 |

All percentages indicated for 6"-OMAL-genistin, 6"-OAC-genistin, 6"-OMAL-daidzin, 6"-OAC-daidzin, glycitin, 6"-OMAL-glycitin, and glycitein are calculated values. The percentages indicated for enzyme concentration are calculated from grams of commercial enzyme preparation per 100 grams solids in each sample.

The following is a description of a method for quantifying isoflavones in soy products. The isoflavones are extracted from soy products by mixing 0.75 gram of sample (spray dried or finely ground powder) with 50 ml of 80/20 methano/water solvent. The mixture is shaken for 2 hours at room temperature with an orbital shaker. After 2 hours, the remaining undissolved materials are removed by filtration through Whatman No. 42 filter paper. Five ml of the filtrate are diluted with 4 ml of water and 1 ml of methanol.

The extracted isoflavones are separated by HPLC (High Performance Liquid Chromatography) using a Hewlett Packard C18 Hypersil reverse phase column. The isoflavones are injected onto the column and eluted with a solvent gradient starting with 88% methanol, 10% water, and 2% glacial acetic acid and ending with 98% methanol and 2% glacial acetic acid. At a flow of 0.4 ml/min, all the isoflavones-genistin, 6"-O- Acetylgenistin, 6"-O-Malonylgenistin, genistein, daidzin, 6"-O-Acetyldaidzin, 6"-O-Malonyldaidzin, daidzin, glycitin and its derivatives and glycitein—are clearly resolved. Peak detection is by UV absorbance at 260 mm. Identification of the peaks was performed by HPLC-mass spectrometer.

Quantification is achieved by using pure standards (genistin, genistein, daidzin and daidzein) purchased from Indofine Chemical Company, Sommerville, N.J. Response factors (integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference.

This method provides the quantities of each individual isoflavone. For convenience, total genistein, total daidzein and total glycitein can be calculated, and represent the aggregate weight of these compounds if all the conjugated forms are converted to their respective unconjugated forms. These totals can also be measured directly by a method using acid hydrolysis to convert the conjugated forms.

The foregoing are merely preferred embodiments of the invention. Various changes and alterations can be made without departing from the spirit and broader aspects thereof as set forth in the appended claims, which are to be interpreted in accordance with the principals of patent law including the Doctrine of Equivalents.

What is claimed is:

1. A method for converting isoflavone conjugates to isoflavone aglucones, comprising:
   forming a mixture comprising isoflavone conjugates and water;
   treating said mixture at a pH of about 6 to about 13.5 and a temperature of about 2° C. to about 121° C. for a time sufficient to convert a majority of said isoflavone conjugates to isoflavone glucones; and
   contacting isoflavone glucones in said mixture with an enzyme capable of cleaving isoflavone glucoside bonds at a pH of about 3 to about 9 and a temperature of about 5° C. to about 75° C. for a time period sufficient to convert said isoflavone glucones to isoflavone aglucones.

2. The method of claim 1 wherein said mixture of isoflavone conjugates and water is treated at a pH of about 9 and a temperature of about 45° C. to about 75° C.

3. The method of claim 1 wherein said mixture of isoflavone conjugates and water is treated at a pH of about 11 and a temperature of about 5° C. to about 50° C.

4. The method of claim 1 wherein said isoflavone glucones contacted with said enzyme are isoflavone glucones converted from said isoflavone conjugates and isoflavone glucones present in said mixture prior to converting said isoflavone conjugates to isoflavone glucones.

5. A method for converting isoflavone conjugates in a vegetable protein material to isoflavone aglucones, comprising:

forming an aqueous slurry of a vegetable protein material containing isoflavone conjugates;

treating said slurry at a pH of about 6 to about 13.5 and a temperature of about 2° C. to about 121° C. for a sufficient time to convert a majority of said isoflavone conjugates to isoflavone glucones;

contacting an enzyme capable of cleaving isoflavone glucoside bonds with isoflavone glucones in said slurry at a pH of about 3 to about 9 and a temperature of about 5° C. to about 75° C. for a time period sufficient to convert said isoflavone glucones in said vegetable protein material to isoflavone aglucones.

6. The method of claim 5, wherein said slurry of vegetable protein material containing isoflavone conjugates is treated at a pH of about 9 and a temperature of about 45° C. to about 75° C.

7. The method of claim 5, wherein said slurry of vegetable protein material containing isoflavone conjugates is treated at a pH of about 11 and a temperature of about 5° C. to about 50° C.

8. The method of claim 5, wherein contacting an enzyme with said isoflavone glucones comprises adding an amount of a supplemental enzyme to said slurry effective to cleave isoflavone glucoside bonds of said isoflavone glucones.

9. The method of claim 8, wherein said supplemental enzyme comprises a saccharaidase enzyme capable of cleaving 1,4-glucoside bonds.

10. The method of claim 9 wherein said supplemental enzyme is selected from the group consisting of alpha-galactosidase enzymes, beta-galactosidase enzymes, glucoamylase enzymes, pectinase enzymes, and combinations thereof.

11. The method of claim 8, wherein said supplemental enzyme is added to said slurry in a concentration of about 0.1% to about 10% by weight of said vegetable protein material, on a dry basis.

12. The method of claim 5 wherein said isoflavone glucones contacted with said enzyme are isoflavone glucones converted from said isoflavone conjugates and isoflavone glucones present in said slurry prior to converting said isoflavone conjugates to isoflavone glucones.

13. The method of claim 5, further comprising separating said isoflavone aglucones from said slurry.

14. The isoflavone product produced by the method of claim 5.

15. A method for converting isoflavone conjugates in vegetable protein material to isoflavone glucones, removing said isoflavone glucones from said vegetable protein material, and converting said isoflavone glucones to isoflavone aglucones comprising:

forming an aqueous slurry of a vegetable protein material containing isoflavone conjugates;

treating said slurry at a pH of about 6 to about 13.5 and a temperature of about 2° C. to about 121° C. for a sufficient time to convert a majority of said isoflavone conjugates to isoflavone glucones;

separating said isoflavone glucones from said vegetable protein material;

forming a mixture of said isoflavone glucones and water;

contacting an enzyme capable of cleaving isoflavone glucoside bonds with isoflavone glucones in said mixture at a pH of about 3 to about 9 and a temperature of about 5° C. to about 75° C. for a time period sufficient to convert said isoflavone glucones to isoflavone aglucones.

16. The method of claim 15, wherein said slurry is treated at a pH of about 9 and a temperature of about 45° C. to about 75° C.

17. The method of claim 15, wherein said slurry is treated at a pH of about 11 and a temperature of about 5° C. to about 50° C.

18. The method of claim 15 wherein said isoflavone glucones separated from said vegetable protein material comprise isoflavone glucones formed by conversion from said isoflavone conjugates and isoflavone glucones present in said vegetable protein material prior to conversion of said isoflavone conjugates to isoflavone glucones.

19. The method of claim 15, wherein contacting an enzyme with isoflavone glucones in said mixture comprises adding an amount of a supplemental enzyme to said mixture effective to cleave isoflavone glucoside bonds of said isoflavone glucones.

20. The method of claim 19, wherein said supplemental enzyme comprises a saccharidase enzyme capable of cleaving 1,4-glucoside bonds.

21. The method of claim 20 wherein said supplemental enzyme is selected from the group consisting of alpha-galactosidase enzymes, beta-galactosidase enzymes, glucoamylase enzymes, pectinase enzymes, and combinations thereof.

22. The method of claim 19 wherein said supplemental enzyme is added to said mixture in a concentration of about 0.1% to about 10% by weight of said vegetable protein material, on a dry basis.

23. The isoflavone aglucone product produced by the method of claim 15.

24. A method for removing isoflavone conjugates and isoflavone glucones from a vegetable protein material and converting said isoflavone conjugates and isoflavone glucones to isoflavone aglucones, comprising:

leaching isoflavone conjugates and isoflavone glucones from a vegetable protein material containing isoflavone conjugates and isoflavone glucones;

forming a mixture of said isoflavone conjugates, said isoflavone glucones, and water;

treating said mixture at a pH of about 6 to about 13.5 and a temperature of about 2° C. to about 121° C. for a sufficient time to convert a majority of said isoflavone conjugates to isoflavone glucones;

contacting an enzyme capable of cleaving isoflavone glucoside bonds with isoflavone glucones in said mixture at a pH of about 3 to about 9 and a temperature of about 5° C. to about 75° C. for a sufficient time to convert said isoflavone glucones to said isoflavone aglucones.

25. The method of claim 24 wherein said leaching is performed at a pH of from about 4 to about 11.

26. The method of claim 24 wherein said leaching is performed at a pH of about 7.

27. The method of claim 24, wherein said mixture of isoflavone conjugates and water is treated at a pH of about 9 and a temperature of about 45° C. to about 75° C. to convert said isoflavone conjugates to isoflavone glucones.

28. The method of claim 24, wherein said mixture of isoflavone conjugates and water is treated at a pH of about 11 and a temperature of about 5° C. to about 50° C. to convert said isoflavone conjugates to isoflavone glucones.

29. The method of claim 24, wherein contacting an enzyme with said isoflavone glucones comprises adding an amount of a supplemental enzyme to said mixture effective to cleave isoflavone glucoside bonds of said isoflavone glucones.

30. The method of claim 29, wherein said supplemental enzyme is a saccharidase enzyme capable of cleaving 1,4-glucoside bonds.

31. The method of claim 30, wherein said supplemental enzyme is selected from the group consisting of alpha-galactosidase enzymes, beta-galactosidase enzymes, gluco- amylase enzymes, pectinase enzymes, and combinations thereof.

32. The method of claim 29, wherein supplemental enzyme is added to said mixture in a concentration of about 0.1% to about 10% by weight of said vegetable protein material on a dry basis.

33. The method of claim 24, further comprising separating said isoflavone aglucones from said mixture.

34. The isoflavone aglucone product produced by the method of claim 24.

* * * * *